US00PP20952P2

(12) United States Plant Patent

Egger

(10) Patent No.: US PP20,952 P2

(45) Date of Patent: Apr. 27, 2010

(54) *AGASTACHE* PLANT NAMED 'SUMMER SKY'

(50) Latin Name: *Agastache hybrid*
Varietal Denomination: Summer Sky

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 12/321,462

(22) Filed: Jan. 20, 2009

(51) Int. Cl.
*A01H 5/00* (2006.01)

(52) U.S. Cl. ..... Plt./399

(58) Field of Classification Search ..... Plt./399
See application file for complete search history.

*Primary Examiner*—Kent L Bell
(74) *Attorney, Agent, or Firm*—Klarquist Sparkman, LLP

(57) ABSTRACT

A new and distinct form of *Agastache* plant characterized by a small, compact habit, violet blue colored flowers in narrow, tight clusters, dark calyces, a low branching habit, a long bloom time, and excellent vigor.

1 Drawing Sheet

Botanical denomination: *Agastache* hybrid.
Variety designation: 'Summer Sky'.
Parentage: *Agastache* sp. 'Pink Pop'×*Agastache rugosa* 'Honey Bee Blue'.

BACKGROUND OF THE INVENTION

The present invention relates to a new and distinct cultivar of *Agastache*, given the name, 'Summer Sky'. *Agastache* is in the family Lamiaceae. This new variety originated from cross was between a dwarf form of *Agastache* sp. 'Pink Pop' (an unpatented plant) as the seed parent and *Agastache rugosa* 'Honey Bee Blue' as the pollen parent. Compared to the seed parent, *Agastache* sp. 'Pink Pop', the new cultivar has violet blue rather than pink flowers. Compared to the pollen parent, *Agastache rugosa* 'Honey Bee Blue' (an unpatented plant), the new cultivar has a much more compact habit, a larger and darker flower, and a less congested inflorescence. Compared to *Agastache* 'Blue Fortune' the new cultivar is shorter.

This plant exhibits the following characteristics that make it unique:

1. Small, compact habit,
2. Violet blue colored flowers in narrow, tight clusters,
3. Dark calyces,
4. A low branching habit,
5. A long bloom time, and
6. Excellent vigor.

The new variety has been reproduced only by asexual propagation (cuttings and micropropagation). Each of the progeny exhibits identical characteristics to the original plant. Asexual propagation by division and micropropagation as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The drawing shows a one-year-old *Agastache* 'Summer Sky' growing in the garden in full sun in late summer in Canby, Oreg.

DETAILED PLANT DESCRIPTION

The following is a detailed description of the new *Agastache* cultivar based on observations of a nine-month-old specimen grown in the greenhouse then planted outside in the ground in May in the trial beds in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The Royal Horticultural Society Colour Chart.

Plant:

*Form.*—Upright, spreading herbaceous perennial
*Cold hardiness.*—USDA Zone 8–9.
*Size.*—Grows to 40 cm wide and 40 cm tall to the top of the flowers.
*Vigor.*—Excellent.
*Stem.*—Square in cross section, grows to 4 mm wide and 35 cm tall, sparsely pubescent, internodes average 4 cm long, Yellow Green 147A.

Leaf:

*Type.*—Simple.
*Arrangement.*—Opposite.
*Shape.*—Ovate.
*Venation.*—Pinnate.
*Margins.*—Crenate.
*Apex.*—Acute.
*Base.*—Cordate.
*Blade size.*—Grows to 32 mm long and 22 mm wide.
*Surface texture.*—Very short hairs on both sides.
*Petiole description.*—14 mm long and 1 mm wide, pubescent, Yellow Green 147B on back or where shaded, Yellow Green 147B tinted Greyed Purple 187A on top side in the sun.
*Leaf color.*—Top side Green 137A, bottom side closest to Yellow Green 147B lightly tinted with Greyed Purple 187A.

Inflorescence:

*Type.*—Terminal spike with 7 to 16 whorls.
*Number of flowers.*—Up to 90 per spike.
*Size of inflorescence.*—7 cm to 17 cm tall and 2 cm wide.

*Peduncle.*—7 cm to 16 cm tall and 2 mm wide, pubescent, Yellow Green 147B.

*Pedicel.*—1 mm to 2 mm long, pubescent, Yellow Green 147B.

*Bloom period.*—June through frost in Canby, Oreg.

Flower bud:

*Size.*—10 mm long and 2 mm wide at the widest point prior to opening.

*Description.*—Tubular.

*Surface texture.*—Pubescent.

*Color.*—Violet 86B.

Flower:

*Type.*—Zygomorphic.

*Shape.*—Bilabiate, tubular.

*Size.*—14 mm long and 4 mm wide.

*Corolla description.*—11 mm long and spreads to 4 mm wide, color outside Violet Blue 90B on top half and 90D on bottom half, inside Violet 86A, pubescent outside and glabrous inside, tube 8 mm long and 1 mm to 3 mm wide; 2 upper lobes joined 2 mm long and 2 mm wide, ovate, acute, entire; three lower lobes, two spreading sideways and curve down slightly, each 1 mm long and 2 mm wide, obtuse, entire; the bottom lobe broad, reflexed, obovate, notched at the tip, entire, 2 mm wide and 2 mm deep.

*Calyx description.*—5 mm long and 1.5 mm wide, pubescent outside and glabrous inside, 5 lobed, lobes narrow, 1 mm long, entire, acuminate, color between Brown 200B and Greyed Purple 187A.

*Pistil description.*—21 mm long, ovary 0.5 mm long, Yellow Green 146C, style 20.5 mm long, stigma and style Violet 86B.

*Stamen description.*—4 in number, paired, filaments 6 mm long, Violet 86B, anthers 0.5 mm long, Greyed Yellow 161D, pollen none.

*Fragrance.*—Light herbal.

*Lastingness.*—A spike blooms for about 3 weeks on the plant.

Fruit: None.

Seed: None, sterile.

Pests and diseases: *Agastache* are known to be susceptible to mildew and rust in dry summer months. The new cultivar has no known resistances but has shown no problems in Canby, Oreg.

I claim:

1. A new and distinct cultivar of *Agastache* plant substantially as shown and described.

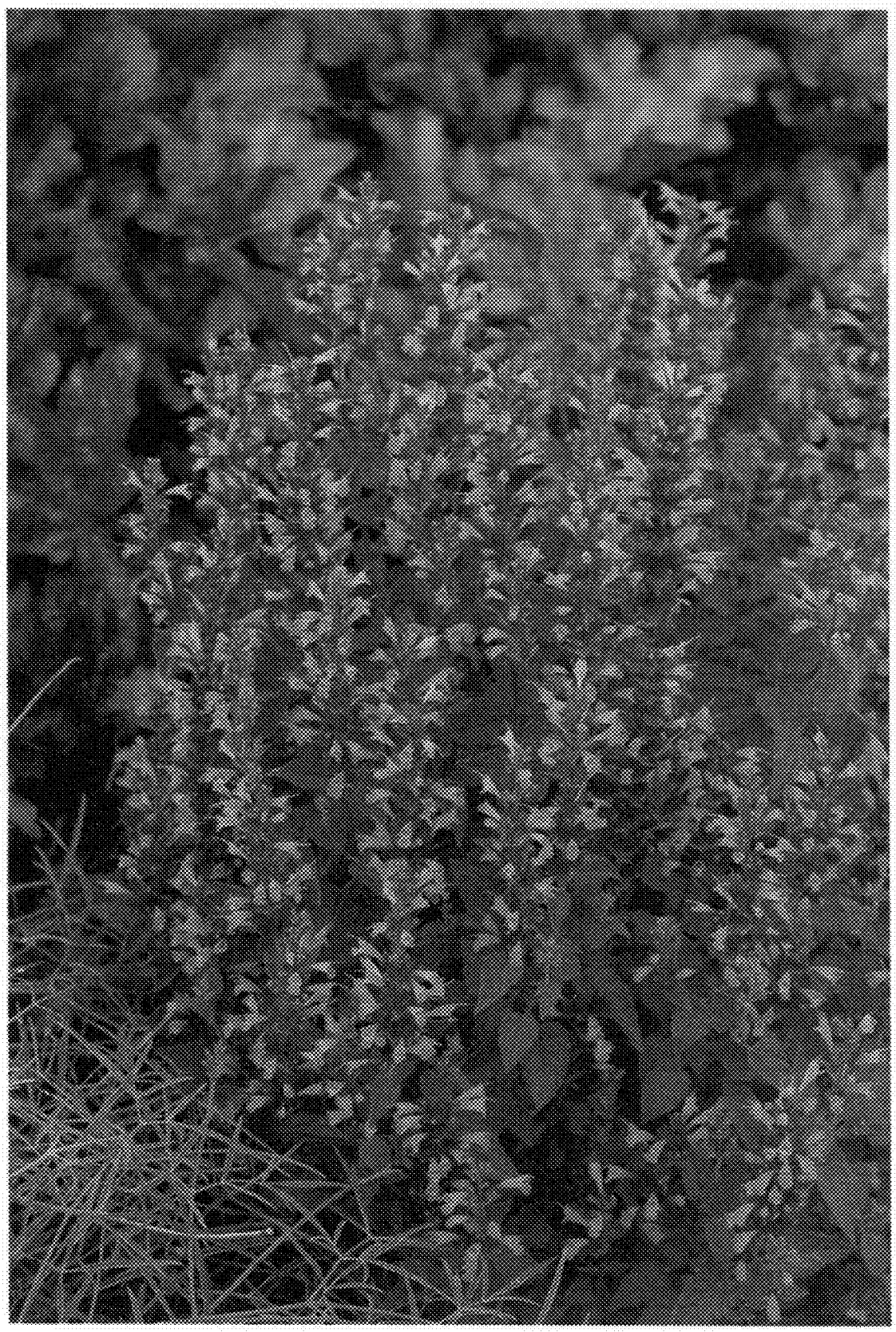

* * * * *